(12) United States Patent
Fournier et al.

(10) Patent No.: US 10,427,990 B2
(45) Date of Patent: Oct. 1, 2019

(54) RECYCLING SYSTEM AND PROCESS OF A METHANOL-TO-PROPYLENE AND STEAM CRACKER PLANT

(71) Applicants: Technip France, Courbevoie (FR); L'Air Liquide, Société Anonyme pour l'Etude et l'Exploitation des Procédés Georges Claude, Paris (FR)

(72) Inventors: Jean-Francois Fournier, Yorba Linda, CA (US); Eric Stanley Wagner, La Canada, CA (US); Jean-Paul Laugier, Paris (FR); Stéphane Haag, Frankfurt am Main (DE); Thomas Wurzel, Oberursel (DE); Martin Gorny, Eschborn (DE)

(73) Assignee: TECHNIP FRANCE, Courbevoie (FR)

( * ) Notice: Subject to any disclaimer, the term of this patent is extended or adjusted under 35 U.S.C. 154(b) by 0 days.

(21) Appl. No.: 15/060,773

(22) Filed: Mar. 4, 2016

(65) Prior Publication Data
US 2017/0253539 A1 Sep. 7, 2017

(51) Int. Cl.
| C07C 1/20 | (2006.01) |
| C07C 4/04 | (2006.01) |
| C07C 11/06 | (2006.01) |
| C10G 9/36 | (2006.01) |

(52) U.S. Cl.
CPC ............... *C07C 1/20* (2013.01); *C07C 4/04* (2013.01); *C07C 11/06* (2013.01); *C10G 9/36* (2013.01); *C10G 2300/104* (2013.01); *C10G 2400/20* (2013.01); *C10G 2400/26* (2013.01); *Y02P 30/42* (2015.11)

(58) Field of Classification Search
CPC ............... C07C 1/20; C07C 4/04; C07C 2/00
See application file for complete search history.

(56) References Cited

U.S. PATENT DOCUMENTS

| 4,478,709 A | * | 10/1984 | Yan ..................... C10G 67/02 208/255 |
| 9,079,813 B2 | * | 7/2015 | Adam ..................... C07C 1/24 |
| 2005/0080308 A1 | * | 4/2005 | Jeong ..................... B01J 27/16 585/653 |
| 2008/0194900 A1 | * | 8/2008 | Bhirud ..................... C10G 9/00 585/648 |
| 2012/0041243 A1 | * | 2/2012 | Senetar ..................... C07C 1/20 585/251 |
| 2012/0041245 A1 | | 2/2012 | Bozzano et al. |

(Continued)

FOREIGN PATENT DOCUMENTS

CN 102190545 A 9/2011

OTHER PUBLICATIONS

Tipler. (2010). The Determination of C2 to C5 Hydrocarbons in Finished Gasolines using the PerkinElmer Clarus 680 GC with Swafer Technology. PerkinElmer, Inc. Shelton, CT.*

(Continued)

*Primary Examiner* — Youngsul Jeong
(74) *Attorney, Agent, or Firm* — Jackson Walker, LLP

(57) ABSTRACT

The present disclosure provides a system and method for recycling intermediate product streams of at least gasoline from the MTP plant to the steam cracker plant for processing with the feedstock of the steam cracker plant to generate a higher percentage of ethylene and propylene. The steam cracker feedstock can be ethane.

16 Claims, 2 Drawing Sheets

(56) References Cited

U.S. PATENT DOCUMENTS

| | | |
|---|---|---|
| 2013/0172627 A1 | 7/2013 | Chewter et al. |
| 2014/0187833 A1* | 7/2014 | Chewter .................. C07C 1/20 585/304 |
| 2015/0148574 A1* | 5/2015 | Chewter .................. C07C 1/20 585/316 |
| 2015/0158783 A1 | 6/2015 | Ramesh |
| 2015/0166430 A1* | 6/2015 | Keusenkothen .......... C07C 4/04 526/75 |

OTHER PUBLICATIONS

US EIA (Glossary. (n.d.) U.S. Energy Information Administration.).*

Kent, J. A. (Ed.). (2013). Handbook of industrial chemistry and biotechnology. Springer Science & Business Media.*

Bergstrom, C., International Search Report for International Patent Application No. PCT/US2017/020653, dated May 23, 2017, European Patent Office.

Pardo Torre, J., Written Opinion for International Patent Application No. PCT/US2017/020653, dated May 23, 2017, European Patent Office.

* cited by examiner

RECYCLING SYSTEM AND PROCESS OF A METHANOL-TO-PROPYLENE AND STEAM CRACKER PLANT

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure generally relates to the production of olefins and recycling specific product streams for greater production and efficiency. More specifically, the disclosure relates to the increased production of ethylene and propylene from a combination of a methanol to propylene (MTP) plant and a steam cracker plant and selective streams for recycling.

Description of the Related Art

Since the early production of olefins based synthetic polymers in the 1950's, the demand has steadily increased. Olefins, including ethylene and propylene, are the raw material for the production of long-chain synthetic polymers that can be created when ethylene and/or propylene gases are polymerized under specific conditions. Historically, steam cracking has been used to break bonds in longer chain molecules using feedstock such as ethane, propane, butane, naphtha and others. In recent years there is a trend to use lighter feedstock, especially ethane, for steam cracking. This trend will result in a shift of the ethylene to propylene ratio towards ethylene and therefore, a driver for on-purpose production of propylene. The art has progressed to using catalytic reactors to produce more propylene than the steam cracking process. For example US Publ. No. 2010/0234655A describes a process known as methanol-to-propylene (MTP) that is able to produce selectively a high amount of propylene by converting oxygenates into hydrocarbons. This technology is a catalytic process to produce on-purpose propylene using natural gas, coal or biomass as feedstocks. These alternative feedstocks are first converted to synthesis gas which is cleaned and then converted to methanol. Methanol in turn is converted to DME (dimethyl ether) which is used to produce a propylene-rich mixture containing various hydrocarbons. These various hydrocarbons are conditioned and fractionated into propylene and other components including ethylene if desired, LPG, and gasoline. From the outset, the MTP process had been based on a tailor made ZSM-5 zeolite catalyst. Efforts then began to combine the two processes.

US Publication No. 2010/0206771 teaches a combination of an MTP process and a steam cracking process. This publication teaches: "For the production of hydrocarbons, in particular C2-C4 olefins, using a combined plant with a steam cracker and at least one reactor for converting an educt mixture which includes steam and at least one oxygenate the respective intermediate product streams of the steam cracker and of the reactor are at least partly combined. To increase the yield of valuable products, a shape-selective zeolite material is used as catalyst in the reactor for oxygenate conversion and at least a part of the product streams obtained downstream of the combined plant is recirculated to the steam cracker and/or the reactor."

US Publication No. 2015/0158783 also teaches a combination. This publication teaches: "The present invention provides an integrated process for the preparation of olefins, which process comprises the steps of: (a) reacting an oxygenate and/or olefinic feed in a reactor to form an effluent which comprises olefins; (b) fractionating at least part of the effluent into two olefinic product fractions; (c) subjecting a hydrocarbon feedstock in a reactor to a steam cracking process to form an effluent which comprises olefins including butadiene; (d) combining at least part of the first olefinic product fraction as obtained in step (b) and at least part of the second effluent which comprises olefins as obtained in step (c) to form a combined olefinic product stream comprising at least ethylene, propylene and butadiene; and (e) separating at least part of the combined olefinic product stream as obtained in step (d) to form a fraction comprising ethylene and/or propylene and a fraction that comprises butadiene."

However, these combinations do not maximize ethylene and propylene regarding the management of the recycling of the different streams produced during the reaction. Therefore, there remains a need to further improve the production of ethylene and propylene from selective recycling of streams in a combined system and process.

BRIEF SUMMARY OF THE INVENTION

The present disclosure provides a system and a method for recycling one or more intermediate product streams of at least gasoline from the MTP plant to the steam cracker plant for processing with the feedstock of the steam cracker plant to generate a higher selectivity of ethylene and propylene. The steam cracker feedstock can be ethane.

In general, an MTP plant rejects by-products rich in paraffins and in particular ethane, propane, and butanes as well as an aliphatic-rich C5/C6/C7+ intermediate process stream. These MTP by-products are converted in a steam cracker plant. This conversion by pyrolysis not only produces additional light olefins, such as ethylene and propylene, but it also increases an olefin-rich C4 cut by-product that is recycled back to the MTP plant. This process is a synergistic process as the olefin-rich recycled stream allows a higher propylene yield in the MTP plant than in the steam cracker plant. The paraffin/aliphatic-rich streams from the MTP plant provide a high light olefins yield in the steam cracker plant. In addition, the ethylene produced by the MTP reactor can be recovered directly in the steam cracker plant as a main olefin product. The MTP reactor and design can be optimized to maximize the combined light olefin production (ethylene and propylene) instead of only maximizing the propylene production. Surprisingly, such an integration results not only in reduced specific investment and utilities, but also in more light olefins than the stand-alone MTP plant or steam cracker plant together.

The by-products from the MTP plant contain some olefins; however, they also contain an important amount of aliphatic components. This composition makes the by-products better suitable for reaction in the steam cracker plant, where aliphatic components can be thermally cracked to light olefins. The by-product streams from the MTP plant can be fed to the steam cracker plant to increase light olefin production by pyrolysis. The MTP plant can flow a C3 intermediate process stream containing light olefin/paraffin products with a carbon number of 3 or less and by-product streams such as a C4 intermediate product stream and a C5/C6/C7+ intermediate process stream to the steam cracker plant for further purification and/or reaction. The streams sent to the steam cracker are advantageously low in oxygenates. The steam cracker plant has a C4 product stream that contains predominately di-olefins and is not suitable to be fed back into the MTP plant without further processing. With selected hydrogenation of the di-olefins, the C4 product becomes a feedstock rich in C4 olefins that can be converted into C2 and C3 olefins in the MTP reactor.

The integration of an MTP plant can be added to an existing steam cracker plant that has undergone a change of feedstock from LPG or naphtha to ethane. Conversely, a steam cracker can be added to an existing MTP plant. In the same way, the intentional joint installation of a steam cracker and an MTP plant is possible.

The disclosure provides a process of producing hydrocarbons from a combined plant made of an oxygenates-to-propylene, preferably a methanol to propylene ("MTP"), plant having at least a catalytic reactor and a steam cracker plant, comprising: flowing a stream having a least a portion of oxygenate into the catalytic reactor; purifying an intermediate process stream from the reactor to reduce oxygenates in a separation section, including gasoline of at least C5 or heavier; flowing at least a portion of the hydrocarbons, including the gasoline, to a cracking furnace; purifying an intermediate process stream from the cracking furnace into at least one process stream having ethylene, and an intermediate process stream of at least C4, C5, or a combination thereof as a cut stream from the separation section; and recycling the cut stream to the catalytic reactor.

The disclosure also provides a process of producing hydrocarbons from a combined plant of an oxygenate-to-propylene, preferably methanol to propylene ("MTP"), plant having at least a catalytic reactor and a steam cracker plant having at least a cracking furnace, comprising: keeping at least the section of effluent intermediate process streams that are purified from the MTP reactor to reduce oxygenates, independent from intermediate process streams that are purified from the cracking furnace; flowing at least one intermediate process stream of at least a portion of MTP plant by-products to the steam cracker plant; converting the MTP plant by-products in the steam cracker plant using thermal pyrolysis to produce ethylene, propylene, or a combination thereof, and a C4 cut by-product containing di-olefins and olefins; selectively hydrogenating the C4 cut by-product containing di-olefins in the steam cracker plant to convert the di-olefins into olefins and increase the C4 olefins content of this stream; and recycling the steam cracker olefin-rich C4 product to the MTP reactor for conversion of the olefins in the C4 product to ethylene, propylene, or a combination thereof, and other MTP reaction by-products, such as propane and pentane, hexane, pentene, and hexene.

The disclosure further provides a system for producing hydrocarbons from a combined plant, comprising: an oxygenate-to-propylene, preferably a methanol to propylene ("MTP"), plant having at least a catalytic reactor and an MTP separation section, the MTP separation section configured to remove oxygenates from at least gasoline; a steam cracker plant having at least a cracking furnace and a cracker separation section; a conduit fluidicly configured to flow the gasoline from the MTP separation section to the cracking furnace, and converting the gasoline in the steam cracker plant using thermal pyrolysis to produce ethylene, propylene, or a combination thereof.

DETAILED DESCRIPTION

Figure 1:
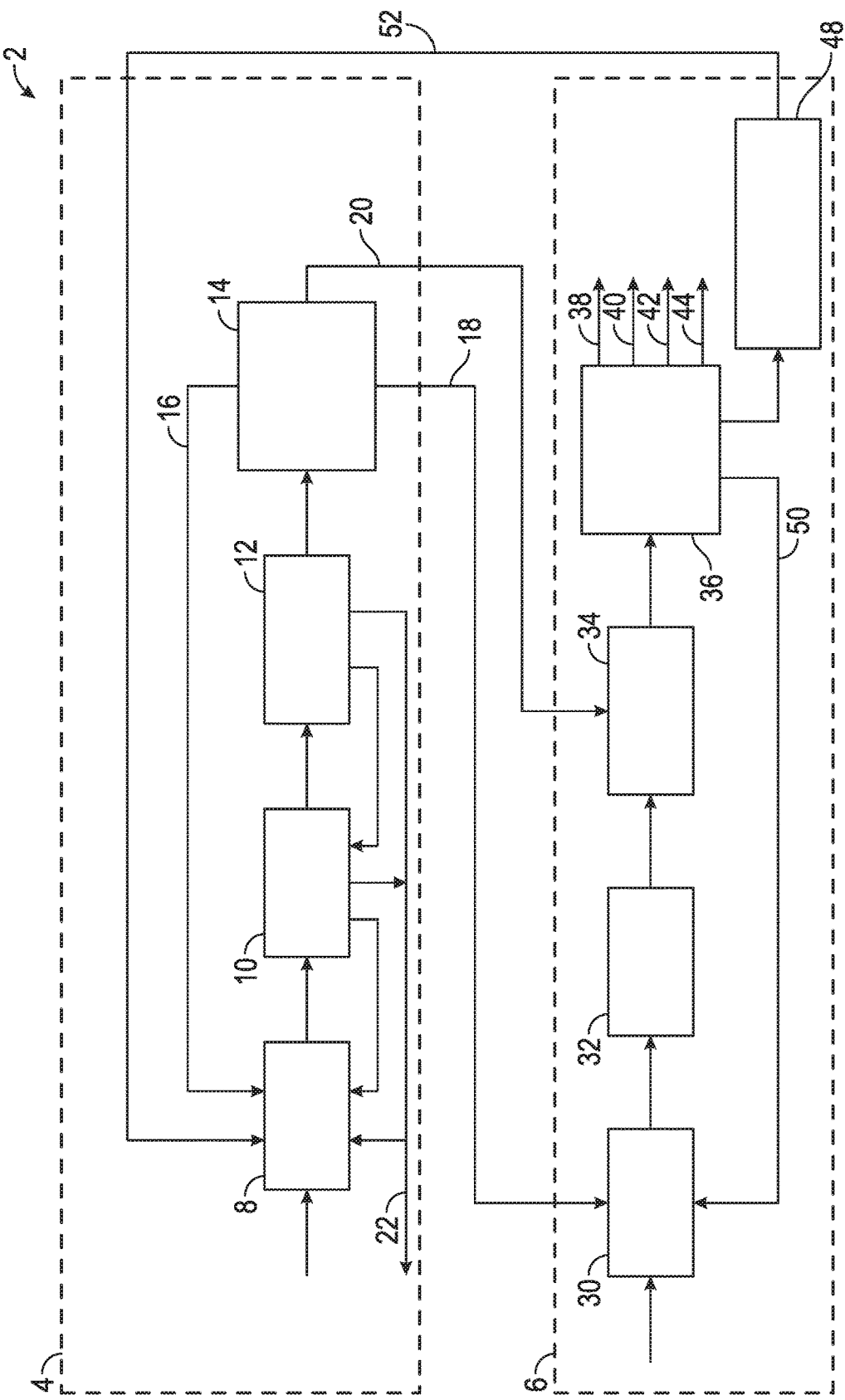
FIG. 1 is an exemplary flowchart for a system and process of a combined methanol-to-propylene (MTP) plant and a steam cracker plant with selective recycled fluids.

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Further, the various methods and embodiments of the system can be included in combination with each other to produce variations of the disclosed methods and embodiments. Discussion of singular elements can include plural elements and vice-versa. References to at least one item may include one or more items. Also, various aspects of the embodiments could be used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions. The term "product stream" means the fluid stream that leaves the MTP plant or the steam cracker plant as a product, such as ethylene, propylene, fuel gas or fuel oil. The term "intermediate product stream" means a fluid stream between components of the system, including those that are recycled between the MTP plant and the steam cracker plant. In some instances, all or a portion of fluid stream can be used as a product or one for recycling. Some elements are nominated by a device name for simplicity and would be understood to include a system or a section, such as a "quencher" would encompass a quenching system or quenching section, and so forth.

The present disclosure provides a system and method for recycling an intermediate product stream of at least gasoline from the MTP plant to the steam cracker plant for processing with the feedstock of the steam cracker plant to generate a higher percentage of ethylene and propylene. The steam cracker feedstock can be ethane.

In at least one embodiment, the process and associated system can be summarized as follows:
combining an MTP plant with a steam cracker plant;
keeping at least the section of the separation section of the MTP reactor effluent streams that removes oxygenates independent from the steam cracker separation section,
converting all or part of the MTP plant by-products (including paraffins, unreacted C4/C5/C6/C7+ olefins, other C4/C5/C6/C7+ aliphatic components, ethane and propane) in the steam cracker plant using thermal pyrolysis to produce light olefins (ethylene and propylene) and C4 and C5 cuts by-products;
selectively hydrogenating the C4 cut by-product (and optionally the C5 cut by-product) in the steam cracker plant to convert di-olefins into olefins and produce an olefin-rich C4 product (and optionally an olefin-rich C5 product); and
recycling the steam cracker olefin-rich C4 product (and optionally the olefin-rich C5 product) to the MTP reactor for conversion of the C4 (and optionally C5) olefins to light olefins (ethylene and propylene).

Advantageously, the operation and design of the MTP plant can be focused on a maximum light olefins production (ethylene and propylene). This focus can include not recycling any stream containing significant amounts of ethylene to the MTP reactor. In other words, the ethylene and propylene productions can be increased by: cracking the MTP by-products in the steam cracker plant and feeding the MTP reactor with the steam cracker C4 (and optionally C5) olefin by-product. The invention will work with: stand-alone MTP plants based on a methanol feed, integrated gas-to-propylene plants (reforming and methanol plant and MTP plants integrated), integrated coal-to-propylene plants (coal gasification, synthesis gas cleaning, methanol synthesis and MTP synthesis integrated), and any other oxygenate to olefin process. Not all products need to be recycled in the described way. Depending on market conditions, the system and process can be modified to selectively produce various percentages (including zero percent) of the exemplary product streams.

FIG. 1 is an exemplary flowchart for a system and process of a combined methanol-to-propylene (MTP) plant and a steam cracker plant with selective recycled fluids. The arrangement could exemplify integrating an olefin-to-propylene plant with a cracker for a retrofit solution. Referring to FIG. 1, the system 2 and associated process includes a portion that functionally can be described as a methanol-to-propylene ("MTP") plant 4 and a portion that functionally can be described as a steam cracker plant 6. The MTP plant is shown as a separate unit from the steam cracker plant. While physical separation is possible, it is envisioned that in at least one embodiment of the combined plant will be integrally connected in operation with each other and thus the demarcation is along functional lines.

Starting with the MTP plant 4, the feedstock, such as methanol, can be provided to a catalytic MTP reactor 8. (To improve operation conditions in the MTP reactor, it may be useful to at least partially convert methanol to DME in a catalytic reactor upstream the MTP reactor, using processes known to those with ordinary skill in the art.) The intermediate process stream from the MTP reactor 8 can flow through a quencher 10 with internal water cycle to cool the stream and condense reaction water and then to a compressor 12. Some of the water from the quencher can be recycled to the MTP reactors. Excess reaction water from the methanol dehydration in the catalytic reactor can be discharged from the quencher 10 into a water stream conduit 22. The quencher removes already some of the oxygenates from the reactor effluent. These are normally recovered from the water for example in a column before it is discharged. The compressor 12 can be a multi-stage compressor that usually has intermediate cooling and partial condensation. Some of the water separated from the condensate in the compressor 12 can be recycled to the quencher 10 and excess water can be discharged into the water stream conduit 22. The intermediate product streams (hydrocarbon vapour and hydrocarbon liquid) from the compressor 12 can be provided to an MTP separation section 14 for a process of fractionation and additional oxygenates removal. The MTP separation section 14 generally includes the fractionation columns and other separation equipment and associated equipment used in the MTP plant to separate the different components in the catalytic reactor effluent into product streams and intermediate product streams. In the MTP separation section, oxygenates can be removed from at least the heavy organic phase (gasoline).

The separation section 14 can also produce a hydrocarbon stream of various hydrocarbons, preferably C4, C5, and/or C6 that can be recycled back through a conduit 16 into the MTP reactor 8. The separation section 14 can separate oxygenates so that the streams sent to the steam cracker plant 6 through conduits 18 and 20 have only trace components of oxygenates that will not harm the steam cracker operation. The oxygenates are recycled back to the MTP reactor. The conduit 18 can flow intermediate process streams C5 and heavier components as gasoline and/or C4 components. The conduit 20 can flow lighter products, C2, or C3, light ends, or a combination thereof as a light end intermediate process stream. In at least one embodiment, the gasoline (and LPG) as an intermediate process stream can be routed to a cracking furnace 30 in the steam cracker plant 6 and added to the primary feedstock ethane that is fed to the cracking furnace 30. Depending on the composition of the intermediate process streams from the MTP plant 4, one or more furnaces other than a cracking furnace for the ethane feedstock may be required to convert the intermediate process streams C5 and heavier. Further, the light end stream of the light ends, C2, C3, or a combination thereof can be directed into a compressor 34 in the steam cracker plant 6 as described above.

Methods for reducing the olefin content in the intermediate process in the MTP plant can vary as would be known to those with ordinary skill in the art and can comprise distillation and extraction steps. Examples of such steps are described in U.S. Pat. No. 8,058,498 and US Application No. 2013/0060073 A1.

The feedstock ethane and the combination of the LPG and gasoline through conduit 18 is at least partially cracked in the cracking furnace 30 and sent to a quencher 32. The intermediate process stream from the separation section 14 of the MTP plant having the light ends and C2s and C3s flows through conduit 20 into the compressor 34. The intermediate process stream in the conduit 20 can be combined with an intermediate process stream from the quencher 32 that flows into the compressor 34. The intermediate product stream from the compressor 34 is sent to a cracker separation section 36. The cracker separation section 36 can include a caustic wash, dryer, C2 hydrogenator, and/or the fractionation columns and other separation equipment and associated equipment used in the steam cracker plant to separate the different components in the cracking furnace effluent into product streams and intermediate product streams. Different functions can be in one or more units that combine for the separation section 36. The product streams from the separation section 36 include a conduit 38 that can flow fuel gas, a conduit 40 that flow ethylene, a conduit 42 that can flow propylene, and a conduit 44 that can flow pyrolysis gasoline ("pygas") and/or fuel oil.

Also, in the separation section 36, the C4 components can be cut in a fractionation step and optionally sent to a hydrogenator 48 as an intermediate process stream forming a cut stream of one or more by-products. The hydrogenator 48 can selectively hydrogenate di-olefins in the C4 intermediate process stream to convert the di-olefins into olefins and increase the C4 olefins content of this stream, thus forming an olefin-rich stream. Such an intermediate process stream can flow via a conduit 52 back to the MTP reactor 8 of the MTP plant 4 to assist in optimizing the selectivity of the streams toward light olefins, in particular propylene. Also, an intermediate process stream of ethane and propane components from the separation section 36 can be recycled through a conduit 50 back to the cracking furnace 30 to mix with the incoming feedstock ethane and the intermediate process stream of gasoline (and LPG), as described above.

Figure 2:
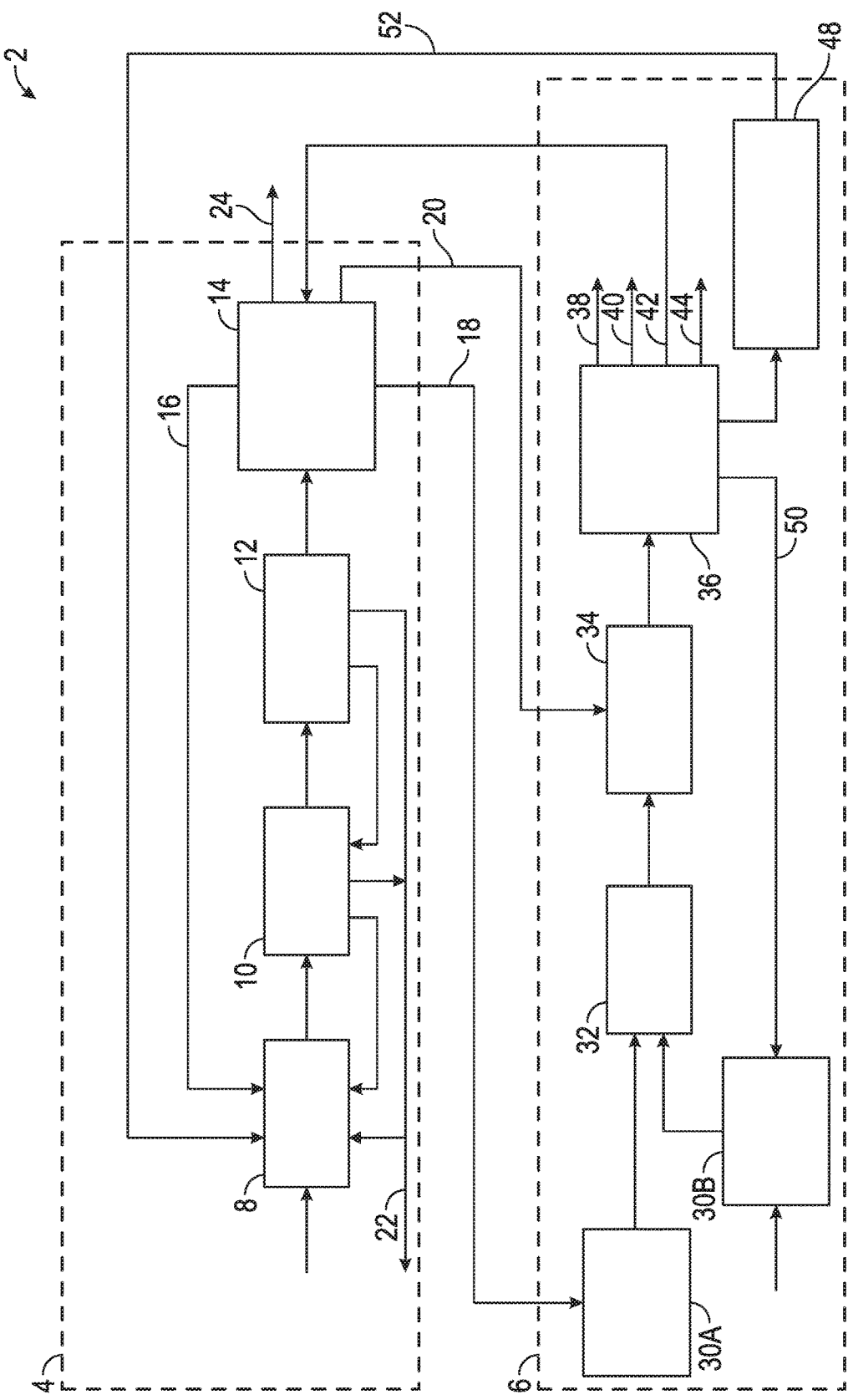
FIG. 2 is another exemplary flowchart for a system and process of a combined methanol-to-propylene (MTP) plant and a steam cracker plant with selective recycled fluids.

FIG. 2 is another exemplary flowchart for a system and process of a combined methanol-to-propylene (MTP) plant and a steam cracker plant with selective recycled fluids. While FIG. 1 shows an exemplary embodiment as a retrofit assembly to existing plants, FIG. 2 shows an exemplary embodiment of a combined system and process that has been designed with the combination in mind. In at least one aspect, the steam cracker unit 6 includes a liquid cracking furnace separate from a gas cracking furnace for more optimization of the recycled intermediate process streams. The system overall is similar to that described for FIG. 1.

In the MTP plant 4, the methanol feedstock, potentially after a first reaction step in a DME prereactor, is delivered to the MTP reactor 8 to produce an intermediate process stream that is quenched in the quencher 10, compressed in the compressor 12, and then purified and depleted from oxygenates in the MTP separation section 14. These steps have been described above for FIG. 1 starting with the MTP plant 4 in a more detail that can be applicable here as well. The separation produces a hydrocarbon stream of C4, C5 and/or C6 that is recycled back through the conduit 16 into the MTP reactor. The separation section 14 produces a process stream through conduit 24 of propylene. The separation section 14 also produces gasoline (and LPG of C3 and/or C4) as an intermediate process stream in the conduit 18 that can be sent to a liquid cracking furnace 30A of the stream cracker plant 6. The LPG in this process can include propane as a lighter fluid than the process in FIG. 1. Also, light ends and C2s from the separation section 14 can flow through the conduit 20 into the compressor 34. The intermediate process stream from the liquid cracking furnace 30A can flow into the quencher 32.

The ethane feedstock is directed into a gas cracking furnace 30B. The intermediate process stream exiting the gas cracking furnace is directed also into the quencher 32 and intermixes with the intermediate process stream from the liquid cracking furnace 30A. The combined quenched streams are sent into the compressor 34 where the combined intermediate process stream is further combined with the intermediate process stream in conduit 20 of light ends and C2s. The combined stream after compression is sent to the cracker separation section 36 that can include a caustic wash, dryer, C2 hydrogenator, and/or one or more fractionation columns. Different functions can be in one or more units that combine for the separation section 36. The product streams from the separation section 36 include a conduit 38 that can flow fuel gas, a conduit 40 that can flow ethylene, and a conduit 44 that can flow pyrolysis gasoline ("pygas") and/or fuel oil. Other products can be used as intermediate process streams for further processing. For example, an intermediate process stream of C3s, such as propane and propylene, from the cracker separation section 36 can be recycled through a conduit 42 back to the MTP separation section 14 in the MTP plant 4. Also, an intermediate process stream of C4 components, including di-olefins, can be cut from the separation section 36 and selectively hydrogenated in the hydrogenator 48 to convert di-olefins into olefins and thus increasing the olefin content of this stream and forming a comparatively olefin-rich C4 product. This stream can then be recycled back through the conduit 52 into the MTP reactor 8. The hydrogenated C4 can be converted in the MTP process into C2 and C3 olefins. Another intermediate process stream generally containing ethane from the separation section 36 can be recycled through the conduit 50 into the gas cracking furnace 30B to combine with the feedstock ethane flowing therein.

The intermediate process stream of C4 components, including di-olefins, generally is the C4 cut typically generated in the separation section of a steam cracker that contains C4 olefins and di-olefins in various concentrations. These concentrations depend significantly on cracker set-up, feedstock, and a potential integration with an olefin to propylene plant. Typical mass concentrations range from 50% of di-olefins for a naphtha liquid cracker to 70% for an ethane gas cracker. The di-olefins can in some cases be extracted as butadiene and form a by-product. For the integration with a MTP plant, it is advantageous to selectively hydrogenate the di-olefins to olefins that react well in the catalytic reactor of the MTP plant and increase light olefin yield. If a butadiene extraction is performed for site-specific reasons, it is possible to send the butadiene-depleted C4 stream, or fractions of it, to the MTP plant.

To describe some of the benefits of the invention, various examples have been calculated using simulation software for the MTP plant 4, and steam cracker plant 6 to compare the stand-alone plants and three steps of integration. For the integration step 1, the light ends and C2's are sent as an intermediate process stream via conduit 20 and the C3 and C4 MTP by-products intermediate process streams are sent through conduit 18 and converted to light olefins by pyrolysis in the steam cracker plant 6. For integration step 2, additionally an MTP by-product, gasoline, is sent as an intermediate process stream through conduit 18 and converted to light olefins by pyrolysis in the steam cracker plant 6. For the integration step 3, in addition to the integration described as step 1 and 2, the steam cracker C4 cut by-product in the C4 hydrogenator 48 is converted to light olefins in the MTP reactor.

The different measures described in the three steps can be combined differently. Not all activities of one step have to be done together and the steps do not have to be staged as described above or in the examples. The optimum solution for each integration heavily depends on the actual design and feedstock of the steam cracker plant and other local conditions.

An MTP—steam cracker integration for a grassroot plant has been studied. As reference, two stand-alone units are considered with middle of run catalysts' conditions and an on-stream factor is 8,400 hours per year.

Three sequential degrees of integration will be applied to a grassroot study case which combines two separate and independent grassroot units:

Lurgi MTP™ unit with a name plate capacity of 1,410 TPD propylene based on 5,000 TPD methanol feed.

Gas Steam Cracker unit, producing 1,000 kTA ethylene, ethane feed, Technip SMK™ cracking furnaces, ethane and propane recycled to extinction.

REFERENCE

The Overall Material Balance for the two stand-alone units is shown in Table 1, considering middle of run catalysts' conditions and an on-stream factor is 8,400 hr/year.

TABLE 1

Stand-alone Steam Cracker + Stand-alone MTP
Overall Material Balance

| Hydrocarbons Products | Cracker kTA | MTP kTA | Total kTA | wt % |
|---|---|---|---|---|
| Ethylene | 1,000 | 26.4 | 1,026 | 50.0% |
| Propylene | 22.5 | 500 | 523 | 25.4% |
| Fuel Gas | 197 | 13.2 | 210 | 10.2% |
| Raw C4 Cut/LPG | 35.8 | 37.2 | 73.0 | 3.6% |
| Pygas/Gasoline | 30.1 | 188 | 218 | 10.6% |
| Fuel Oil | 3.9 | — | 3.9 | 0.2% |
| Total Hydrocarbons | 1,289 | 765 | 2,054 | 100% |

Integration Step 1:

In this step:

the MTP C2s and lighter are sent to the steam cracker plant upstream of the caustic wash, the cracker C3 cut is sent to the separation section 14 in the MTP unit, The propane from the separation section 14, which now combines the propane generated in the MTP reactor and the propane generated in the steam cracker furnaces, is mixed with the MTP C4s. This C3/C4 mixture, which has also been subjected to enhanced oxygenate recovery, is sent to the cracking furnaces in the steam cracker plant.

With this configuration, the MTP C2s and light ends are recovered and fractionated in the steam cracker plant. In the end, the MTP ethane and the MTP LPG (C3/C4) are used as a supplemental feed to the cracking furnaces.

Integration Step 2:

In a second integration step further to the integration described in step 1, the MTP gasoline is sent to the steam cracker plant to feed a liquid cracking furnace, using Technip GK6® coil technology in this study case. Since the MTP gasoline contains very low amounts of di-olefins, no partial or full hydrogenation of the stream is required prior to feeding it to the cracking furnace. Once-through steam cracking yields evaluated with Technip's SPYRO® software show that approximately 30% of the MTP gasoline can be directly converted to light olefins. In a stand-alone MTP plant, the gasoline product is normally used as low sulfur blend stock for gasoline pools. A further improvement of the gasoline conversion to light olefins could be achieved through hydrogenation of the MTP gasoline before feeding it to the steam cracker plant. This hydrogenation step to convert olefins into paraffins could be done to further increase the cracking yields to ethylene and propylene.

Integration Step 3

In a third integration step, the olefin-rich streams from the steam cracker plant are sent to the MTP reactor for conversion to propylene, using preferably the C4 cut from the steam cracker plant. In general, conversion of the C4 cut is in competition with other potential uses of the stream, such as extraction of butadiene or recycle of the C4 stream to the cracking furnaces. For the third integration step, the recycle of the full C4 cut after partial hydrogenation of the di-olefins is shown. One or more other olefin-rich streams from the steam cracker plant can also be used as feed to the MTP reactor as well, provided the stream does not contain significant amounts of di-olefins or aromatics.

Integration Steps Results:

Compared to two stand-alone units, the first integration step leads to a slightly lower propylene production. While this result may seem surprising, it is actually in line with a preference of increasing the light olefins production. It is a deliberate result from design simplifications made in the integrated MTP unit. The integration step 3 can boost the light olefins production (ethylene+propylene) by almost 10% while reducing the quantity of by-products by nearly 30%.

TABLE 2

MTP - Steam Cracker Integration
Grassroot Study Case
Integration Steps Summary

| Products kTA | Stand-alone 1 + 1 | Step 1 | Step 2 | Step 3 |
|---|---|---|---|---|
| Ethylene | 1,026 | 1,086 | 1,120 | 1,132 |
| Propylene | 523 | 507 | 533 | 556 |
| Total Light Olefins | 1,549 | 1,593 | 1,653 | 1,688 |
|  |  | +3% | +7% | +9% |
| Fuel Gas | 210 | 218 | 237 | 245 |
| Raw C4 Cut/LPG | 73 | 36 | 54 | 0 |
| including Butadiene | 24.8 | 25.5 | 33.3 | 0 |
| Pygas/Gasoline | 218 | 203 | 80 | 88 |
| Fuel Oil | 4 | 4 | 30 | 33 |
| Total By-Products | 505 | 461 | 401 | 366 |
|  |  | −9% | −21% | −28% |
| Total Hydrocarbons | 2,054 | 2,054 | 2,054 | 2,054 |

Other and further embodiments utilizing one or more aspects of the invention described above can be devised without departing from the spirit of Applicant's invention. For example, the processes and system can be varied to produce various percentages of some products over other products, along with other variations can occur in keeping within the scope of the claims.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope or range of equivalents of the following claims.

What is claimed is:

1. A process of producing hydrocarbons from a combined plant of a methanol-to-propylene ("MTP") plant having at least a catalytic reactor and a steam cracker plant, the process comprising the steps of:
    flowing a stream having at least a portion of methanol and dimethyl ether into the catalytic reactor to produce a first intermediate process stream containing propylene, C4+ oxygenates, and gasoline;
    purifying the first intermediate process stream from the catalytic reactor in a separation section of the MTP plant to produce an oxygenate recycle stream, a propylene stream, and a gasoline stream, wherein the gasoline stream comprises oxygenate-reduced C5 or heavier components;
    flowing at least a portion of the gasoline stream from the separation section of the MTP plant to a steam cracking furnace, without passing through a catalytic reactor, that converts gasoline to ethylene by non-catalytic pyrolysis thereby producing a second intermediate process stream containing at least ethylene and a C4 di-olefin fraction; and
    purifying the second intermediate process stream from the steam cracking furnace into a product process stream having ethylene in a cracker separation section.

2. The process of claim 1, further comprising producing product process streams of ethylene, propylene, fuel gas, and fuel oil, pygas, or a combination thereof.

3. The process of claim 1, wherein the composition of the gasoline stream remains constant as the gasoline stream flows from the separation section of the MTP plant to the steam cracking furnace.

4. The process of claim 1, wherein the process further comprises steps of separating ethane and propane from the second intermediate process stream during the step of purifying the second intermediate process stream and recycling the ethane and propane to the steam cracking furnace.

5. The process of claim 1, wherein the steam cracking furnace comprises a liquid cracking furnace and a gas cracking furnace, wherein the process further comprises:
    flowing the gasoline stream into the liquid cracking furnace and flowing an ethane feedstock stream into the gas cracking furnace; and
    combining intermediate process streams from the liquid cracking furnace and the gas cracking furnace.

6. The process of claim 1, wherein the first intermediate process stream further comprises a liquefied petroleum gas ("LPG") fraction having at least C3 hydrocarbons, C4 hydrocarbons, or a combination thereof, wherein the step of purifying the first intermediate process stream further comprises a step of producing an LPG stream, and the process further comprises the step of flowing the LPG stream into the steam cracking furnace with the gasoline stream.

7. The process of claim 1, wherein the first intermediate process stream further comprises a light end fraction containing C2 hydrocarbons, C3 hydrocarbons, or a combination thereof, wherein the step of purifying the first intermediate process stream further comprises a step of producing a light end stream, wherein the process further comprises a step of flowing the light end stream to a compressor downstream of the steam cracking furnace to mix with the second intermediate process stream from the steam cracking furnace.

8. A process of producing hydrocarbons from a combined plant of a methanol-to-propylene ("MTP") plant having at least an MTP catalytic reactor and a steam cracker plant having at least a steam cracking furnace, the process comprising the steps of:
    keeping at least a portion of effluent intermediate process streams that are purified from the MTP catalytic reactor to reduce oxygenates independent from intermediate process streams that are purified from the steam cracking furnace;
    obtaining an MTP plant by-products having at least oxygenate-reduced C5 hydrocarbons or heavier components from the portion of effluent intermediate process streams that are purified from the MTP catalytic reactor in a separation section;
    flowing at least a portion of the MTP plant by-products having at least oxygenate-reduced C5 hydrocarbons or heavier components from the separation section to the steam cracker plant, without passing through a catalytic reactor, that converts gasoline to ethylene; and
    converting the at least a portion of the MTP plant by-products in the steam cracker plant (SCP) under conditions effective for thermal non-catalytic pyrolysis to produce an SCP intermediate process stream comprising ethylene and C4 di-olefins;
    purifying the SCP intermediate process stream to produce an ethylene stream and a C4 di-olefin stream;
    hydrogenating the C4 di-olefin stream to produce a C4 olefin stream; and
    recycling the C4 olefin stream to the MTP catalytic reactor wherein C4 olefins within the C4 olefin stream are converted to propylene within the MTP catalytic reactor.

9. The process of claim 1, wherein the purifying the second intermediate process stream further comprises separating at least one intermediate process stream of at least C4 hydrocarbons, C5 hydrocarbons, or a combination thereof as a second cut stream from the cracker separation section; and
    the process further comprises recycling the second cut stream to the catalytic reactor.

10. The process of claim 9, further comprising hydrogenating at least a portion of the second cut stream.

11. The process of claim 1, further comprising an absence of a step of hydrogenating the gasoline stream prior to the step of flowing at least a portion of the gasoline stream to the steam cracking furnace.

12. The process of claim 1, further comprising a step of hydrogenating the gasoline stream prior to the step of flowing at least a portion of the gasoline stream to the steam cracking furnace.

13. The process of claim 1, wherein the second intermediate process stream has a volumetric flow rate greater than that of the at least a portion of the gasoline stream flowed to the steam cracking furnace.

14. The process of claim 1, wherein the second intermediate process stream is derived from the gasoline stream flowed to the steam cracking furnace and a separate ethane stream introduced to the steam cracking furnace.

15. The process of claim 7, wherein during the step of purifying the second intermediate process stream, a first cut stream comprising the C4 di-olefin fraction is formed, wherein the process further comprises steps of hydrogenating the first cut stream to produce a C4 olefin stream; and recycling the C4 olefin stream to the catalytic reactor of the MTP plant, wherein C4 olefins are converted to propylene within the catalytic reactor, thereby increasing propylene content of the first intermediate process stream.

16. A process for producing hydrocarbons from a combined plant of methanol-to-propylene ("MTP") plant having at least an MTP catalytic reactor and a steam cracker plant, the process comprising the steps of:
  introducing a feed stream comprising methanol and dimethyl ether ("DME") to the MTP catalytic reactor under conditions effective for producing a first intermediate process stream containing propylene, C4+ oxygenates, a light ends fraction, and gasoline, wherein the light end fraction comprises C2 hydrocarbons, C3 hydrocarbons, or a combination thereof;
  separating the first intermediate process stream using a fractionator into a propylene stream, an oxygenate recycle stream containing the C4+ oxygenates, a light end stream, and a gasoline stream;
  recycling the C4+ oxygenate stream to the MTP catalytic reactor;
  introducing the gasoline stream along with an ethane feedstock to a steam cracker furnace under conditions effective for producing a second intermediate process stream containing ethylene and a C4 di-olefin fraction, wherein the gasoline stream is introduced from the fractionator to the steam cracker furnace without passing through a catalytic reactor;
  compressing the light end stream and the second intermediate process stream and then introducing the light end stream and the second intermediate process stream into a cracker separation unit;
  withdrawing a fuel gas stream, an ethylene stream, a propylene stream, a pygas stream, a C2 hydrocarbon and C3 hydrocarbon stream, and a C4 di-olefin stream from the cracker separation unit;
  hydrogenating the C4 di-olefin stream in a hydrogenator under conditions effective for producing a C4 olefins stream; and
  recycling the C4 olefins stream to the MTP catalytic reactor, wherein C4 olefins are converted to propylene within the MTP catalytic reactor, thereby increasing propylene content of the first intermediate process stream.

\* \* \* \* \*